(12) United States Patent
Faram

(10) Patent No.: US 7,909,033 B2
(45) Date of Patent: Mar. 22, 2011

(54) BREATHING TREATMENT APPARATUS

(75) Inventor: Joseph Dee Faram, Dallas, TX (US)

(73) Assignee: Comedica Incorporated, Dallas, TX (US)

( * ) Notice: Subject to any disclaimer, the term of this patent is extended or adjusted under 35 U.S.C. 154(b) by 973 days.

(21) Appl. No.: 11/743,770

(22) Filed: May 3, 2007

(65) Prior Publication Data

US 2007/0256690 A1 Nov. 8, 2007

Related U.S. Application Data

(60) Provisional application No. 60/746,355, filed on May 3, 2006.

(51) Int. Cl.
*F16K 31/02* (2006.01)
*B67D 7/00* (2010.01)

(52) U.S. Cl. ......... 128/204.21; 128/204.18; 128/204.25; 222/3; 222/299

(58) Field of Classification Search ............. 128/203.12, 128/203.16, 204.14, 204.18, 204.21, 204.25; 222/3, 299
See application file for complete search history.

(56) References Cited

U.S. PATENT DOCUMENTS

| | | | |
|---|---|---|---|
| 402,779 A | 5/1889 | Steinhoff | |
| 1,150,238 A | 8/1915 | Winbray | |
| 3,083,707 A | 4/1963 | Seeler | |
| 3,291,122 A | 12/1966 | Engstrom et al. | |
| 3,301,255 A | 1/1967 | Thompson | |
| 3,537,448 A | 11/1970 | Liston | |
| 3,561,444 A | 2/1971 | Boucher | |
| 3,584,621 A * | 6/1971 | Bird et al. ................ 128/200.18 |
| 3,861,386 A | 1/1975 | Harris et al. | |
| 4,054,134 A | 10/1977 | Kritzer | |
| 4,062,358 A | 12/1977 | Kritzer | |
| 4,182,599 A | 1/1980 | Eyrick et al. | |
| 4,245,633 A | 1/1981 | Erceg | |
| 4,436,090 A | 3/1984 | Darling | |
| 4,558,710 A | 12/1985 | Eichler | |
| 4,601,465 A | 7/1986 | Roy | |
| 4,635,857 A | 1/1987 | Hughes | |
| 4,770,164 A | 9/1988 | Lach et al. | |
| 4,951,659 A | 8/1990 | Weiler et al. | |
| 4,964,404 A | 10/1990 | Stone | |
| 4,973,047 A | 11/1990 | Norell | |
| 4,981,295 A | 1/1991 | Belman et al. | |
| 5,018,517 A | 5/1991 | Liardet | |
| 5,027,809 A | 7/1991 | Robinson | |
| 5,067,707 A | 11/1991 | Køhnke | |
| 5,069,449 A | 12/1991 | Wardwell | |
| 5,107,830 A | 4/1992 | Younes | |
| 5,127,400 A | 7/1992 | DeVries et al. | |
| 5,150,291 A | 9/1992 | Cummings et al. | |
| 5,193,529 A | 3/1993 | Labaere | |
| 5,261,394 A | 11/1993 | Mulligan et al. | |
| 5,277,175 A | 1/1994 | Riggs et al. | |

(Continued)

*Primary Examiner* — Justine R Yu
*Assistant Examiner* — Valerie Skorupa
(74) *Attorney, Agent, or Firm* — Barnes & Thornburg LLP

(57) ABSTRACT

The present invention relates to a method and apparatus for treating a variety of breathing disorders experienced by patients. The invention is particularly suited to the treatment of atelectasis, the partial or total collapse of the lung, although those skilled in the art will appreciate that it has applications in treating other disorders as well. Treating patients with breathing disorders traditionally has required the use of multiple types of apparatus in order to provide the multiple types of treatment used. The present invention provides for a treatment apparatus that is enabled to provide multiple types of treatment, depending on the needs of the patient.

24 Claims, 3 Drawing Sheets

U.S. PATENT DOCUMENTS

| | | |
|---|---|---|
| 5,322,057 A | 6/1994 | Raabe et al. |
| 5,355,873 A | 10/1994 | Del Bon et al. |
| 5,390,665 A | 2/1995 | Leach |
| 5,398,676 A | 3/1995 | Press et al. |
| 5,413,110 A | 5/1995 | Cummings et al. |
| 5,423,313 A | 6/1995 | Olsson et al. |
| 5,439,430 A | 8/1995 | Rubens et al. |
| 5,451,190 A | 9/1995 | Liardet |
| 5,535,738 A | 7/1996 | Estes et al. |
| 5,542,416 A | 8/1996 | Chalvignac |
| 5,547,440 A | 8/1996 | Rubens et al. |
| 5,570,682 A * | 11/1996 | Johnson .................. 128/200.14 |
| 5,598,839 A | 2/1997 | Niles et al. |
| 5,617,847 A | 4/1997 | Howe |
| 5,664,562 A | 9/1997 | Bourdon |
| 5,666,945 A | 9/1997 | Davenport |
| 5,713,349 A | 2/1998 | Keaney |
| 5,823,179 A | 10/1998 | Grychowski et al. |
| 5,829,429 A | 11/1998 | Hughes |
| 5,906,198 A | 5/1999 | Flickinger |
| 5,937,857 A | 8/1999 | Caterini et al. |
| 5,938,117 A | 8/1999 | Ivri |
| 5,950,619 A | 9/1999 | Van Der Linden et al. |
| 5,964,223 A | 10/1999 | Baran |
| 5,970,974 A | 10/1999 | Van Der Linden et al. |
| 6,044,841 A | 4/2000 | Verdun et al. |
| 6,058,932 A | 5/2000 | Hughes |
| 6,076,519 A | 6/2000 | Johnson |
| 6,076,520 A | 6/2000 | Cooper |
| 6,079,413 A | 6/2000 | Baran |
| 6,085,740 A | 7/2000 | Ivri et al. |
| 6,085,746 A | 7/2000 | Fox |
| 6,116,233 A | 9/2000 | Denyer et al. |
| 6,152,134 A * | 11/2000 | Webber et al. ........... 128/205.24 |
| 6,167,881 B1 | 1/2001 | Hughes |
| 6,210,345 B1 | 4/2001 | Van Brunt |
| 6,234,167 B1 | 5/2001 | Cox et al. |
| 6,240,919 B1 | 6/2001 | MacDonald et al. |
| 6,289,892 B1 | 9/2001 | Faithfull et al. |
| 6,302,105 B1 | 10/2001 | Wickham et al. |
| 6,336,455 B1 | 1/2002 | Howlett |
| 6,340,025 B1 | 1/2002 | Van Brunt |
| 6,355,002 B1 | 3/2002 | Faram et al. |
| 6,363,932 B1 | 4/2002 | Forchione et al. |
| 6,402,046 B1 | 6/2002 | Loser |
| 6,405,934 B1 | 6/2002 | Hess et al. |
| 6,412,481 B1 | 7/2002 | Bienvenu et al. |
| 6,415,791 B1 | 7/2002 | Van Brunt |
| 6,425,393 B1 | 7/2002 | Lurie et al. |
| 6,427,690 B1 | 8/2002 | McCombs et al. |
| 6,450,163 B1 | 9/2002 | Blacker et al. |
| 6,467,476 B1 | 10/2002 | Ivri et al. |
| 6,526,976 B1 | 3/2003 | Baran |
| 6,540,153 B1 | 4/2003 | Ivri |
| 6,540,154 B1 | 4/2003 | Ivri et al. |
| 6,546,927 B2 | 4/2003 | Litherland et al. |
| 6,550,472 B2 | 4/2003 | Litherland et al. |
| 6,550,476 B1 | 4/2003 | Ryder |
| 6,557,549 B2 | 5/2003 | Schmidt et al. |
| 6,568,387 B2 | 5/2003 | Davenport et al. |
| 6,571,790 B1 | 6/2003 | Weinstein |
| 6,581,596 B1 | 6/2003 | Truitt et al. |
| 6,581,598 B1 | 6/2003 | Foran et al. |
| 6,581,600 B2 * | 6/2003 | Bird ........................ 128/205.24 |
| 6,588,421 B1 | 7/2003 | Diehl et al. |
| 6,588,422 B1 | 7/2003 | Berthon-Jones et al. |
| 6,595,203 B1 | 7/2003 | Bird |
| 6,598,602 B1 | 7/2003 | Sjoholm |
| 6,598,603 B1 | 7/2003 | Andersson et al. |
| 6,609,517 B1 | 8/2003 | Estes et al. |
| 6,612,303 B1 | 9/2003 | Grychowski et al. |
| 6,615,831 B1 | 9/2003 | Tuitt et al. |
| 6,626,175 B2 | 9/2003 | Jafari et al. |
| 6,631,721 B1 | 10/2003 | Salter et al. |
| 6,640,806 B2 | 11/2003 | Yurko |
| 6,644,304 B2 | 11/2003 | Grychowski et al. |
| 6,644,310 B1 | 11/2003 | Delache et al. |
| 6,644,311 B1 | 11/2003 | Truitt et al. |
| 6,663,574 B2 | 12/2003 | Faram et al. |
| 6,679,258 B1 | 1/2004 | Strom |
| 6,694,969 B1 | 2/2004 | Heinonen et al. |
| 6,702,998 B2 | 3/2004 | Conner |
| 6,708,688 B1 | 3/2004 | Rubin et al. |
| 6,718,969 B1 | 4/2004 | Rubin et al. |
| 6,722,362 B2 | 4/2004 | Hete et al. |
| 6,729,334 B1 | 5/2004 | Baran |
| 6,737,042 B2 | 5/2004 | Rabinowitz et al. |
| 6,752,151 B2 | 6/2004 | Hill |
| 6,776,159 B2 | 8/2004 | Pelerossi et al. |
| 6,805,120 B1 | 10/2004 | Jeffrey et al. |
| 6,823,866 B2 | 11/2004 | Jafari et al. |
| 6,848,443 B2 | 2/2005 | Schmidt et al. |
| 6,851,425 B2 | 2/2005 | Jaffre et al. |
| 6,854,462 B2 | 2/2005 | Berthon-Jones et al. |
| 6,904,906 B2 | 6/2005 | Salter et al. |
| 6,907,881 B2 | 6/2005 | Suki et al. |
| 6,910,479 B1 | 6/2005 | Van Brunt |
| 6,915,803 B2 | 7/2005 | Berthon-Jones et al. |
| 6,932,084 B2 | 8/2005 | Estes et al. |
| 6,948,497 B2 | 9/2005 | Zdrojkowski et al. |
| 6,968,840 B2 | 11/2005 | Smith et al. |
| 7,011,091 B2 | 3/2006 | Hill et al. |
| 7,036,500 B2 | 5/2006 | Niles et al. |
| 7,059,324 B2 | 6/2006 | Pelerossi et al. |
| 7,066,176 B2 | 6/2006 | Jaffe et al. |
| 7,070,761 B2 | 7/2006 | Rabinowitz et al. |
| 7,100,607 B2 | 9/2006 | Zdrojkowski et al. |
| 7,128,069 B2 | 10/2006 | Farrugia et al. |
| 7,165,547 B2 | 1/2007 | Truitt et al. |
| 7,188,621 B2 | 3/2007 | DeVries et al. |
| 7,191,776 B2 | 3/2007 | Niles et al. |
| 7,191,780 B2 | 3/2007 | Faram |
| 7,204,245 B2 | 4/2007 | Johnson et al. |
| 7,210,480 B2 | 5/2007 | Lurie et al. |
| 7,232,417 B2 | 6/2007 | Plante |
| 7,302,949 B2 | 12/2007 | Pelerossi et al. |
| 7,445,607 B2 | 11/2008 | Plante |
| 7,469,700 B2 | 12/2008 | Baran |
| 7,472,702 B2 | 1/2009 | Beck et al. |
| 7,472,705 B2 | 1/2009 | Baran |
| 7,500,481 B2 | 3/2009 | Delache et al. |
| 7,562,657 B2 | 7/2009 | Blanch et al. |
| 7,600,511 B2 | 10/2009 | Power et al. |
| 7,699,054 B2 | 4/2010 | Pelerossi et al. |
| 2001/0004893 A1* | 6/2001 | Biondi et al. ............. 128/204.18 |
| 2002/0020412 A1* | 2/2002 | Gilbert et al. ............. 128/203.12 |
| 2003/0051731 A1 | 3/2003 | Be'eri et al. |
| 2003/0140925 A1 | 7/2003 | Sapienza et al. |
| 2003/0205229 A1 | 11/2003 | Crockford et al. |
| 2005/0061318 A1* | 3/2005 | Faram ...................... 128/204.18 |
| 2005/0109340 A1 | 5/2005 | Tehrani |
| 2005/0165334 A1 | 7/2005 | Lurie |
| 2005/0217666 A1* | 10/2005 | Fink et al. ................. 128/200.14 |
| 2006/0084877 A1* | 4/2006 | Ujhazy et al. ................. 600/483 |
| 2006/0144398 A1 | 7/2006 | Doshi et al. |
| 2006/0178245 A1 | 8/2006 | Schiller et al. |
| 2006/0201500 A1 | 9/2006 | Von Hollen et al. |
| 2006/0243274 A1 | 11/2006 | Lieberman et al. |
| 2006/0272642 A1 | 12/2006 | Chalvignac |
| 2007/0017522 A1 | 1/2007 | Be-Eri et al. |
| 2007/0017523 A1 | 1/2007 | Be-Eri et al. |
| 2007/0089740 A1 | 4/2007 | Baumert et al. |
| 2007/0186928 A1 | 8/2007 | Be-Eri |
| 2008/0000475 A1 | 1/2008 | Hill |
| 2008/0000477 A1 | 1/2008 | Huster et al. |
| 2008/0015456 A1 | 1/2008 | McCawley et al. |
| 2008/0091117 A1 | 4/2008 | Choncholas et al. |
| 2008/0190429 A1 | 8/2008 | Tatarek |
| 2008/0283060 A1 | 11/2008 | Bassin |
| 2009/0020121 A1 | 1/2009 | Bassin |

\* cited by examiner

BREATHING TREATMENT APPARATUS

CROSS-REFERENCE TO RELATED APPLICATION

This application claims the benefit of priority from U.S. Provisional Application No. 60/746,355 filed on May 3, 2006.

FIELD OF THE INVENTION

The invention relates to a therapeutic breathing device that delivers multiple therapies in order to facilitate the prevention and treatment of certain pulmonary diseases.

BACKGROUND OF THE INVENTION

Atelectasis is the partial or total collapse of the lung. Although this condition may occur as a result of pressure being exerted from outside the lungs by such maladies as a tumor or fluid buildup in the pleural space, it is most often caused by obstruction within the airways. When blockage develops the air in the small air sacs, or alveoli, on the distal side of the obstruction is absorbed into the bloodstream and the air sacs become diminished in size or collapse. These alveoli then often fill with blood cells, mucus, or serum, making them highly susceptible to infection. Atelectasis may happen suddenly or gradually manifest over a long period of time. In either case the disorder may lead to shortness of breath, decreased oxygen levels, increased heart rate, and infection, which in turn can result in outcomes ranging from simple discomfort to death.

Traditionally, prevention and treatment of atelectasis have included a wide variety of devices that facilitate treatment in three main areas: 1) medicated aerosol delivery, 2) lung expansion therapy, and 3) secretion clearance therapy. The variety of devices used in these therapies presents a number of problems. First, for any given patient it is difficult to know in advance which therapy or combination of therapies is most appropriate. After assessing the patient at bedside, the clinician may decide that the patient requires a different therapy than planned, at which point he or she must return to a supply room to secure the proper therapy device or devices. This can be time consuming and can delay treatment at a time when prompt application of treatment is crucial. Second, in order to be prepared to deliver appropriate therapy, the healthcare provider must stock a number of devices, which presents the provider with the requirements of storage space and the need to deal with a number of suppliers. Furthermore, maintaining a number of different devices, and their attendant disposable accessories, to provide multiple therapy options increases costs to the healthcare provider and ultimately the patient. Third, in order to adequately utilize various devices a clinician must attend multiple training sessions, further increasing costs to the healthcare provider and patient.

Thus, there has been a need for a single apparatus which is capable of delivering a number of different breathing therapies, thereby eliminating the need for multiple devices, but which is also cost effective and does not significantly increase the time required to train operators in its use.

SUMMARY OF THE INVENTION

The present invention combines aerosol delivery, lung expansion therapy, and secretion clearance therapy into a single apparatus. In one aspect of the present invention, aerosol delivery can be combined with either pulsatile gas flow to provide a secretion clearance mode, or with a linear gas flow to provide a lung expansion mode. A third mode of operation is also disclosed in which linear gas flow without aerosol delivery is provided to the patient. The apparatus is comprised of a gas control box and a patient interface circuit. The gas control box controls the flow of gas from the gas source to the patient interface circuit. The patient interface circuit may be of single patient use and utilizes a fixed venturi and orifices open to the atmosphere for entrainment. The circuit also includes an exhalation opening which can be adjusted to maintain a positive pressure in the lungs at the end of exhalation (Positive End Expiratory Pressure or PEEP) without the stacking of successive volumes of gas in the airways (breath stacking). PEEP helps to open the airways and keep them open during the therapy. The apparatus is designed to minimize both clinical training requirements and operator errors during treatment. Additionally, with several therapies combined into one machine, the clinician can change therapies as needed without having to return to an equipment storage area to retrieve other devices. Storage requirements are reduced and the healthcare provider can deal with a single source vender for supplies, training, and repairs. It is expected that the healthcare provider would also achieve significant cost savings through the reduction in the number of different types of equipment required to perform the various treatments performed by the current apparatus.

BRIEF DESCRIPTION OF THE DRAWINGS

The invention will be better understood with reference to the drawings taken in connection with the detailed description which follows.

DETAILED DESCRIPTION

The present invention relates to a method and apparatus for treating a variety of breathing disorders experienced by patients. The invention is particularly suited to the treatment of atelectasis, the partial or total collapse of the lung, although those skilled in the art will appreciate that it has applications in treating other disorders as well. In a patient suffering from atelectasis, the lung can become partially or completely deflated due to fluid buildup, or from physical pressure such as from a trauma or tumor. If this occurs, the lung may not be able to re-inflate on its own, which can in turn exacerbate the patient's condition leading to a progressively worsening physical state or even death.

Treating a patient with atelectasis traditionally has required the use of multiple types of apparatus in order to provide the multiple types of treatment used. The present invention provides for a treatment apparatus that is enabled to provide multiple types of treatment, depending on the needs of the patient.

Figure 1:
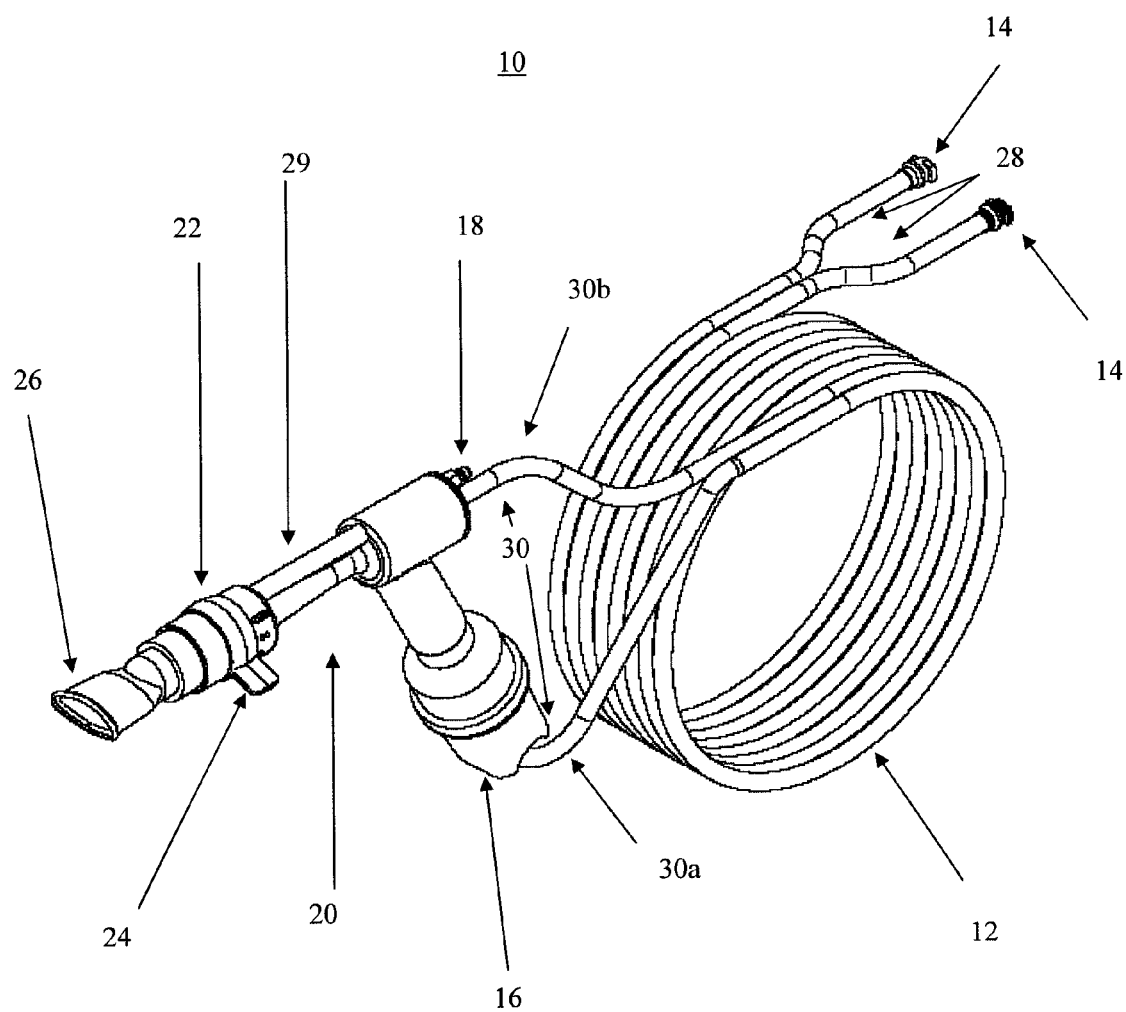
FIG. 1 is a view of the Patient Interface Circuit of the present invention.
Figure 2:
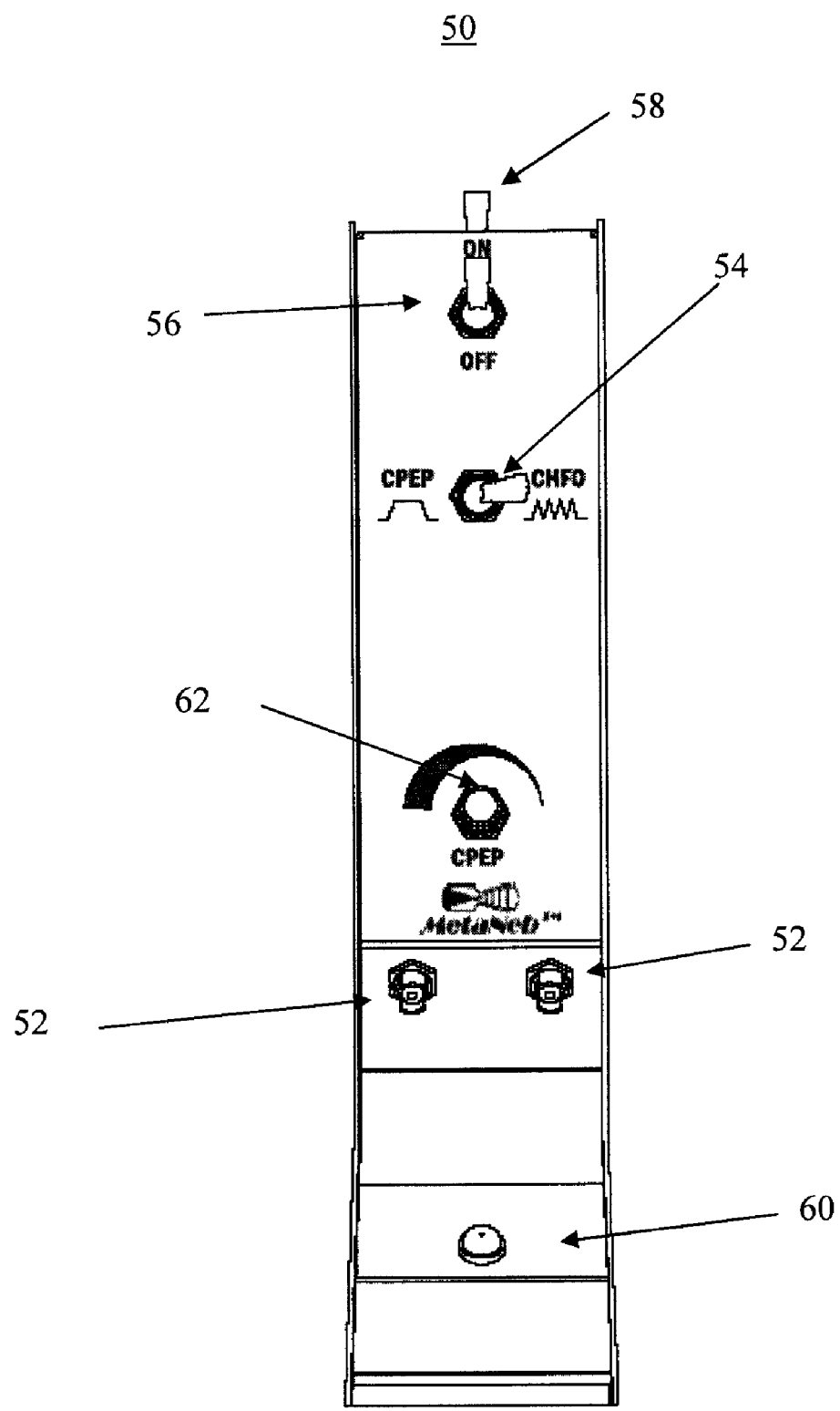
FIG. 2 is an elevation view of the front face of the Gas Control Box of the present invention.
Figure 3:
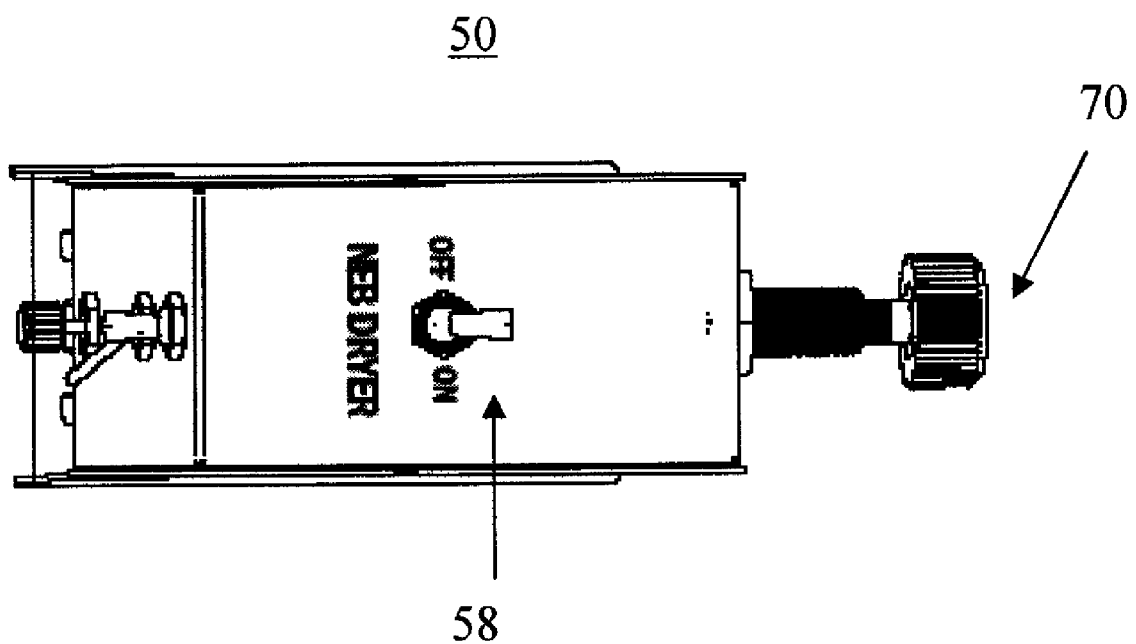
FIG. 3 is a top-down view of the Gas Control Box of the present invention.

Referring to FIGS. 1, 2, and 3, the invention is comprised generally of a patient interface circuit 10, and a gas control box 50. Patient interface circuit 10 is fluidly connected to gas control box 50 and provides transportation of breathing treatment gas (not shown) from gas control box 50 to the patient (not shown). In a first embodiment, patient interface circuit 10 is comprised of a length of tubing 12 having first and second ends 28 and 30, a nebulizer 16, a manometer port 18, and handset 20, a selector ring 22 with a selector ring tab 24 and a mouthpiece 26. Tubing 12 is of medical grade quality of a type commonly available from medical supply houses. One or more connectors 14 may be used to enable first end 28 of tubing 12 to be removably connected to one or more circuit connectors 52 located on gas control box 50. However, the connectors 14 are not required in the event that tubing 12 is to be permanently connected to gas control box 50, or if gas control box 50 is fitted with a type of connector which is capable of interfacing with the ends of tubing 12 in such a way as to create a substantially gas tight connection between first end 28 of tubing 12 and gas control box 50. In a preferred embodiment, tubing 12 is double stranded, in that it is made up of two separate gas conduits that are longitudinally attached to each other, but which are not in fluid communication. Such tubing is commonly known as paratubing. If connectors 14 are used, one connector is required for each gas conduit, thus in the preferred embodiment, the connectors 14 and circuit connectors 52 may be color coded to assist the operator in making the correct connections between connectors 14 and circuit connectors 52 at gas control box 50.

Second end 30 of tubing 12 is fluidly connected to nebulizer 16 and provides gas flow which is used to entrain medicine or other substances contained within the nebulizer. Nebulizer technology is well known in the art and does not need to be recounted here. Examples of nebulizer technology may be seen at U.S. Pat. No. 6,929,003, Nebulizer Apparatus and Method, and U.S. Pat. No. 6,748,945, Nebulizer Apparatus and Method.

In an embodiment wherein tubing 12 is paratubing, the ends 30*a* and 30*b* of second end 30 may be separated and attached to nebulizer 16 at one or more entry points, or may bypass nebulizer 16 altogether. For example, first end 30*a* may enter nebulizer 16 at a point wherein the gas flowing from tubing 12 is used to aerosolize liquid medication held within nebulizer 16, while a second end may enter handset 20 at a point where it is directed through handset 20 so that it may entrain aerosolized medication so that it may be delivered to the patient. While the disclosed embodiment describes the invention as including nebulizer 16, it should be apparent to one skilled in the art that nebulizer 16 is not required for all applications and that the invention disclosed includes embodiments wherein nebulizer 16 is excluded.

In the preferred embodiment, gas exits nebulizer 16 and flows into handset 20, although, if nebulizer 16 is excluded, gas will flow directly from tubing 12 into handset 20. Once in handset 20, gas is entrained into an integral venturi, and then continues out mouthpiece 26 where it is inhaled by the patient. As the patient exhales back into mouthpiece 42 some of the exhalation gas exits an exhalation port (not shown). The exhalation port may be made larger or smaller by adjusting selection collar 22 using exhalation collar tab 24. In a preferred embodiment, proximal pressure is transmitted from patient back through pressure sensing tube 29, which is connected to manometer port 18. Pressure can be monitored by connecting a manometer (not shown) to manometer port 18.

Turning to FIGS. 2 and 3, FIG. 2 shows a front view perspective of gas control box 50, which may be enabled to regulate the flow of gas to the patient. Specifically, gas control box 50 may comprise one or more control devices of the type commonly known in the art such as valves, control interfaces, flow regulators, and the like. Patient interface circuit 20 is connected to gas control box 50 at one or more connectors 52. In a preferred embodiment, to begin a breathing therapy session, the clinician selects one of one or more breathing treatment modes depending on the condition of the patient. In the preferred embodiment shown, the clinician may select from between lung expansion CPEP™ mode (Continuous Positive Expiratory Pressure) or secretion mobilization CHFO™ mode (Continuous High-frequency Oscillation) although those skilled in the art will recognize that alternative therapies could be selected without deviating from the scope and content of the present invention. Mode selection is accomplished by moving mode selector switch 54 to the desired setting. The therapy is initiated by moving master switch 56 from the "off" position to the "on" position. After the therapy has been turned on the patient may begin the therapy by placing his or her mouth onto mouthpiece 26 and breathing normally.

If CPEP™ mode has been chosen, the gas flow is linear. The rate of flow can be adjusted by moving CPEP™ control knob 62. In the embodiment shown, counterclockwise rotation of control knob 62 results in increased flow, while clockwise rotation would decrease the gas flow. Other types of control mechanisms such as sliders, switches and digital interfaces could be substituted without deviating from the scope of the invention. Furthermore, the direction of movement of the control mechanism is not critical, and other variations would be within the scope of the invention.

IF CHFO™ mode has been chosen, gas flow is pulsatile in nature at substantially constant amplitude. In a preferred embodiment, gas flow is regulated or adjusted so that it is pulsitile at a rate of from 1 to 15 hertz at substantially constant amplitude.

Following the desired amount of time in therapy, master switch 56 is returned to the "off" position and patient interface circuit 20 may be disconnected.

In an alternative embodiment, gas control box 50 may be equipped with a nebulizer dryer spray nozzle. If a nebulizer 16 has been used in therapy, it may be desirable to reuse nebulizer 16 rather than simply discarding it. If nebulizer 16 is to be reused, however, it should be cleaned and dried prior to reuse. The clinician, or other operator, would thus wash nebulizer 16 in any of a number of known ways, including using soap and water. Following cleaning and/or rinsing, nebulizer 16 may be dried by moving nebulizer dryer switch 58 to the "on" position. This sends a flow of gas through dryer spray nozzle 60. Nebulizer 16 is held in front of spray nozzle 60 until it is dry. Neb dryer switch 58 is returned to the "off" position.

FIG. 3 shows a top view perspective of gas control box 50. Source gas connector 70 is connected to an appropriate gas source such as compressed air or oxygen.

Additional embodiments of the present invention are also possible. In another embodiment, a means for preventing inadvertent occlusion of the exhalation ports such as guards or screens positioned so as to prevent inadvertent blockage of the ports while still allowing gas flow through the ports.

In another embodiment, means for tracking patient use of the apparatus is included. Such means for tracking use would include any means whereby the identity of the individual using the apparatus may be tracked as well as the duration and type of treatment received. Such means could be as simple as printed records requiring patient acknowledgement that he or she received treatment, more complex means such as digital identification media capable of interfacing with the apparatus in such a way that the apparatus could identify the patient and then record treatment particulars itself.

In another embodiment, the described apparatus can be connected to, and be incorporated into, a ventilator circuit.

In another embodiment, the apparatus includes a means for supplying its own compressed gas rather than relying on an external gas source. Such means could include means for receiving and/or storing containers of compressed gas, or onboard compressor means for creating compressed gas.

In another embodiment, the disclosed apparatus includes means for measuring and/or displaying data concerning the treatment provided. Such means could include digital or analog gauges or displays and could be used to display pressure or flow rate at any point along patient interface circuit 10 or within gas control box 50. Means for measuring and displaying gas flow rate and pressure are well known in the art and will not be recounted herein.

In another embodiment, the apparatus includes means for displaying waveforms, such as a monitor.

In another embodiment, the apparatus includes means for transmitting and receiving data, either wirelessly or wired.

In another embodiment, the patient interface circuit is disposable.

In another embodiment, the apparatus includes means for collecting and analyzing data. As will be appreciated by those having skill in the art, many methods and devices may be used to collect and analyze data, such as sensors and computer systems.

What is claimed:

1. A breathing treatment apparatus comprising:
    a source of gas under pressure capable of providing substantially continuous positive gas flow;
    regulator means for regulating the flow of said substantially continuous positive gas flow between said source and a patient;
    selector means for selecting between one or more modes of operation, including at least a first mode of operation and a second mode of operation;
    means for interrupting said continuous positive gas flow;
    a patient interface circuit having one or more apertures open to the ambient to allow ingress and egress of flow and calibrated to allow patient exhalation and prevent stacking of successive volumes of gas in the airway of the patient, the patient interface circuit further having a removable nebulizer, a venturi tube fluidly connected to said one or more apertures, and a means for covering a portion of said one or more apertures to restrict ingress and egress of flow; and
    a gas control box housing the regulator means and the means for interrupting, the housing carrying the selector means, the housing having a first connector to which the source of gas couples, the housing having at least one second connector to which the patient interface circuit couples, and the housing having a nebulizer dryer nozzle through which gas is expelled to dry the nebulizer when the nebulizer is removed from the patient interface circuit.

2. The apparatus of claim 1, further comprising an aerosol entrainment port fluidly connectable to said nebulizer for entrainment of aerosol.

3. The apparatus of claim 1, wherein said means for interrupting said continuous positive gas flow is capable of interrupting said continuous positive gas flow at a rate of at least 1 hertz and at most 15 hertz whereby the gas flow becomes pulsatile with a substantially constant pressure amplitude.

4. The apparatus of claim 1, wherein in at least one of said one or more modes of operation, the patient is provided with interrupted gas flow.

5. The apparatus of claim 4, further comprising a nebulizer and an aerosol entrainment port fluidly connectable to said nebulizer for entrainment of aerosol.

6. The apparatus of claim 5, wherein the patient is provided with interrupted gas flow and entrained aerosol.

7. The apparatus of claim 1, wherein in at least one of said one or more modes of operation, the patient is provided with linear gas flow.

8. The apparatus of claim 7, further comprising an aerosol entrainment port fluidly connectable to said nebulizer for entrainment of aerosol.

9. The apparatus of claim 8 wherein the patient is provided with linear gas flow and entrained aerosol.

10. The apparatus of claim 1, wherein the flow of said substantially continuous positive gas flow between said source and said patient is controlled by said regulator means.

11. The apparatus of claim 1, wherein the means for interrupting said continuous positive gas flow is operator adjustable in order to achieve a desirable rate at which the flow of said continuous positive gas flow is interrupted.

12. The apparatus of claim 1, further including a means to prevent inadvertent occlusion of said apertures.

13. The apparatus of claim 1, further including a means for tracking use of said apparatus, whereby patient compliance with breathing therapy can be ascertained.

14. The apparatus of claim 1, wherein said patient interface circuit is connected to and incorporated within a ventilator circuit.

15. The apparatus of claim 1, wherein said gas under pressure comprises a container of compressed gas.

16. The apparatus of claim 1, wherein said patient interface circuit includes a port connectable to a pressure manometer.

17. The apparatus of claim 1, further including a means for measuring pressure.

18. The apparatus of claim 1, further including a means for displaying pressure.

19. The apparatus of claim 1, further including a means for displaying waveforms.

20. The apparatus of claim 1, further including a means for collecting data.

21. The apparatus of claim 1, further including a means analyzing data.

22. The apparatus of claim 1, further including a communications port for at least one of transmitting and receiving data.

23. The apparatus of claim 1, further including a nebulizer dryer switch coupled to the gas control box and movable to an "on" position to send a flow of gas through the nebulizer dryer nozzle.

24. The apparatus of claim 1, wherein said patient interface circuit is for single patient use.

* * * * *